(12) United States Patent
Heymsfield et al.

(10) Patent No.: US 6,468,209 B1
(45) Date of Patent: Oct. 22, 2002

(54) METHOD AND APPARATUS FOR ESTIMATING BODY FAT

(75) Inventors: Steven B. Heymsfield, Mt. Kisco, NY (US); Tamotsu Iwabuchi; Miyuki Kodama, both of Tokyo (JP)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/579,014

(22) Filed: May 26, 2000

Related U.S. Application Data

(60) Provisional application No. 60/136,378, filed on May 27, 1999.

(51) Int. Cl.[7] ................................................. A61B 5/00
(52) U.S. Cl. ...................................... 600/300; 128/897
(58) Field of Search ................................ 600/547, 587, 600/300–301; 128/828, 897; 177/245

(56) References Cited

U.S. PATENT DOCUMENTS

| | | | | |
|---|---|---|---|---|
| 5,415,176 A | * | 5/1995 | Sato et al. | 600/547 |
| 5,615,689 A | * | 4/1997 | Kotler | 600/547 |
| 5,827,734 A | * | 10/1998 | Weigle et al. | 435/325 |
| 6,010,454 A | * | 1/2000 | Arieff et al. | 600/309 |
| 6,063,051 A | * | 5/2000 | Stern | 604/27 |

OTHER PUBLICATIONS

Mouroux et al., Contribution of Echotomography to the Study of Excess Fat and its Incidence in Metabolic Complications in Women, Dec. 11, 1986, Semaine des Hopitaux de Paris, pp. 3591–3595.*

Healthy percentage body fat ranges: an approach for developing guidelines based on body mass index; pp. 694–701, Authors: (Dympna Gallaghr, Steven B. Heymsfield, Moonseong Heo, Susan A.Jebb, Peter R. Murgatroyd and Yoichi Sakamoto).

* cited by examiner

*Primary Examiner*—Kevin Shaver
*Assistant Examiner*—Michael C Astorino
(74) *Attorney, Agent, or Firm*—McDermott, Will & Emery

(57) ABSTRACT

The body fat percentage for a person is estimated from the BMI of the person by employing a multiple regression analysis using the reciprocal of the BMI (1/BMI) as the independent variable. In other embodiments, potentially independent and easily obtained variables such as age, sex, and ethnicity are also used in conjunction to provide precise estimates of the body fat percentage. Devices for estimating the body fat percentage can be implemented as calculators, smart scales, and Internet web sites.

31 Claims, 13 Drawing Sheets

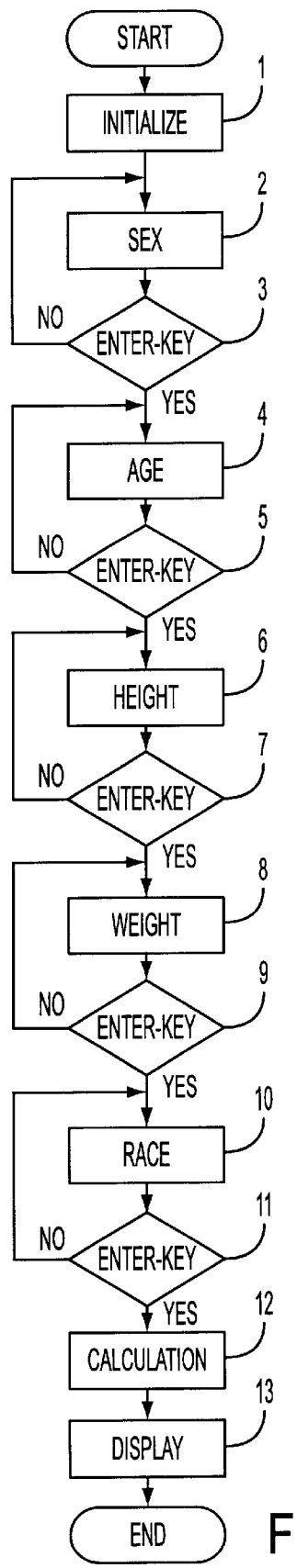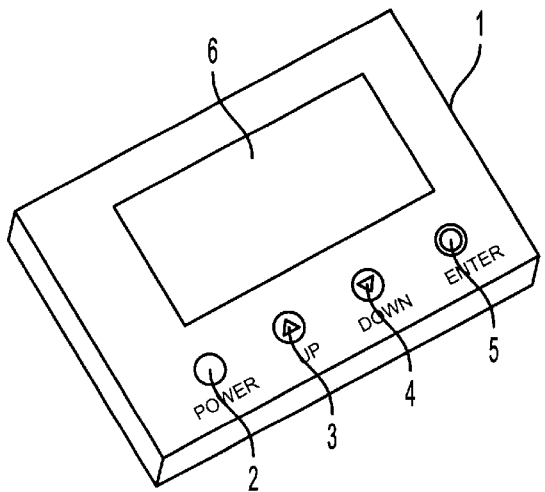
FIG. 1
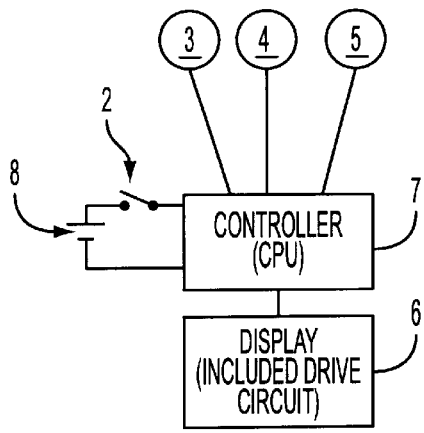
FIG. 2
FIG. 3

FIG. 4A

AGE: 25
HEIGHT: 170cm
WEIGHT: 55Kg
RACE: ASIAN WHITE BLACK
BMI:
FAT: %
FAT: Kg
400

FIG. 4B

AGE: 25
HEIGHT: 170cm
WEIGHT: 55Kg
RACE: ASIAN WHITE BLACK
BMI:
FAT: %
FAT: Kg
402

FIG. 4C

AGE: 27
HEIGHT: 170cm
WEIGHT: 55Kg
RACE: ASIAN WHITE BLACK
BMI:
FAT: %
FAT: Kg
404

FIG. 4D

AGE: 27
HEIGHT: 165cm
WEIGHT: 55Kg
RACE: ASIAN WHITE BLACK
BMI:
FAT: %
FAT: Kg
406

FIG. 4E

AGE: 27
HEIGHT: 165cm
WEIGHT: 53Kg
RACE: ASIAN WHITE BLACK
BMI:
FAT: %
FAT: Kg
408

FIG. 4F

AGE: 27
HEIGHT: 165cm
WEIGHT: 53Kg
RACE: ASIAN
BMI:
FAT: %
FAT: Kg
410

FIG. 4G

AGE: 27
HEIGHT: 165cm
WEIGHT: 53Kg
RACE: ASIAN
BMI: 19.5
FAT: %
FAT: Kg
412

FIG. 9A

AGE: 25  
BMI:  
HEIGHT: 160cm  
FAT: %  
WEIGHT: 0Kg  
FAT: Kg  
RACE: ASIAN WHITE BLACK  
900

FIG. 9B

AGE: 25  
BMI:  
HEIGHT: 160cm  
FAT: %  
WEIGHT: 0Kg  
FAT: Kg  
RACE: ASIAN WHITE BLACK  
902

FIG. 9C

AGE: 27  
BMI:  
HEIGHT: 160cm  
FAT: %  
WEIGHT: 0Kg  
FAT: Kg  
RACE: ASIAN WHITE BLACK  
904

FIG. 9D

AGE: 27  
BMI:  
HEIGHT: 165cm  
FAT: %  
WEIGHT: 0Kg  
FAT: Kg  
RACE: ASIAN WHITE BLACK  
906

FIG. 9E

AGE: 27  
BMI:  
HEIGHT: 165cm  
FAT: %  
WEIGHT: 0Kg  
FAT: Kg  
RACE: ASIAN  
908

FIG. 9F

AGE: 27  
BMI:  
HEIGHT: 165cm  
FAT: %  
WEIGHT: 53Kg  
FAT: Kg  
RACE: ASIAN  
910

FIG. 9G

AGE: 27  
BMI: 19.5  
HEIGHT: 165cm  
FAT: %  
WEIGHT: 53Kg  
FAT: Kg  
RACE: ASIAN  
912

METHOD AND APPARATUS FOR ESTIMATING BODY FAT

RELATED APPLICATION

The present application claims the benefit of U.S. Provisional Patent Application Ser. No. 60/136,378 entitled METHOD AND APPARATUS FROM DETERMINING BODY FAT PERCENTAGE FROM A BODY MASS INDEX, filed on May 27,1999, the contents of which are hereby incorporated by reference in their entirety.

FIELD OF THE INVENTION

The present invention relates to artificial intelligence and more particularly to a method and apparatus for estimating body fat percentage of a person

BACKGROUND OF THE INVENTION

With the steady increase in worldwide rates of obesity, the National Institutes of Health (NIH) and the World Health Organization (WHO) have recently adopted similar body weight standards for diagnosing overweightness and obesity. For example, a person is considered overweight according to these standards if the person's body weight adjusted for height, referred to a body weight index (BMI=weight/height$^2$), is greater than 25 kg/m$^2$ and obese if the BMI is greater than 30 kg/m$^2$. Conversely, being underweight is defined as having a BMI less than 18.5 kg/m$^2$. Practitioners have been using these body weight guidelines in diagnosing the presence of excessive adiposity and prescribing treatment for their overweight patients.

Lately, there has been increasing interest in quantifying a person's total body fat or the person's body fat percentage rather than BMI as a direct measure of obesity. The main assumption of the BMI standards is that body mass, adjusted for stature, is associated with body fatness and consequent morbidity and mortality. However, there some individuals who are overweight according to the BMI standards, but not overfat (e.g. body builders), Similarly, there are some lean individuals such as marathon runners who are not "underweight" in accordance with the BMI standards but who have a very low body fat content Due to the variations among the population, there is at present no accepted consensus on how BMI and body fat are linked.

Accordingly, several approaches have been developed for measuring body fat, but all of these approaches require special equipment. For example, am underwater or hydrostatic weighing technique compares a person's weight in air and the person's weight in water and, taking the person's lung volume into account, computes the person's body volume and density The body fat percentage is then estimated from the calculated body density. This technique, however, requires special equipment for weighing a person .underwater such as stainless steel water tanks.

Another body fat measurement technique is known as "dual energy X-ray absorptiometry" (DXA), in which a person is irradiated with X-rays to measure the bone mineral content and body fat percentage by differences in the X-ray absorption rates. This technique, too, requires special equipment to produce and measure the X-rays. Still another technique includes drinking heavy water comprising D$_2$O or $^3$H$_2$O and calculating the deuterium or tritium dilution to determine the total body water, from which the body fat percentage can be estimated. This approach require special ingredients, equipment, and expertise.

Bioelectronic impedance analysis (BIA) can also be used to estimate body fat percentage from measuring the electrical impedance of a person and correlating the impedance with the person's standing height and body weight In contrast with the previous techniques, the BIA can be performed with relatively inexpensive pieces of equipment.

In all of these techniques, however, some additional equipment is required, ranging from the X-ray machines to bioelectronic impedance measurement devices. here is a need for a method and apparatus for estimating the body fat percentage, which is simple to apply and does not require special equipment or expertise. In fact, there is a need for a technique that can be performed over the Internet without requiring the user to purchase special equipment.

SUMMARY OF THE INVENTION

These and other needs are addressed by the present invention in which the body fat percentage for a person is estimated from the BMI of the person. The present invention stems from the discovery that the models for body fat percentage can be developed using a multiple regression analysis with the reciprocal of the BMI (1/BMI) as the independent variable. Use of the 1/BMI terms advantageously linearizes the data and avoids the need for logarithmic conversion or inclusion of power terms and therefore simplifies the computing apparatus and programs. Preferably, other potentially independent and easily obtained variables such as age, sex, and ethnicity are also used to provide precise estimates of the body fat percentage. All of such variables can readily be determined without the use of special equipment or expertise.

One aspect of the invention relates to an apparatus, a machine-implemented method, and software for estimating a body fat percentage of a person put indicating data concerning the person is received, and the body fat percentage of the person is then estimated based on a reciprocal of a body mass index (BMI), which is the quotient of the weight of the person divided by the square of the height of the person. Then the estimated body fat percentage is output to the user, Various embodiments of the apparatus include a body fat calculator, a personal computer programmed to estimate body fat percentage, a web server that provides a web site for estimating body fat percentages, and a scale that is equipped to weigh a person and use the measured weight to estimate the body fat percentage.

Still other objects and advantages of the present invention will become readily apparent from the following detailed description, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 1 depicts a body fat calculator in accordance with one embodiment of the present invention.

FIG. 2 depicts an electrical block diagram of the body At calculator depicted in FIG. 1.

FIG. 3 is a flowchart illustrating the operation using the body fat calculator depicted in FIG. 1.

FIGS. 4(a), 4(b), 4(c), 4(d), 4(e), 4(f), and 4(g) depict screens displayed by the body fat calculator depicted in FIG. 1.

FIGS. 9(a), 9(b), 9(c), 9(d), 9(e), 9(f), and 9(g) depict screens displayed in another mode by the scale depicted in FIG. 5.

DESCRIPTION OF THE PREFERRED EMBODIMENT

Methods and apparatuses for estimating body fat percentage are described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

CONCEPTUAL OVERVIEW

In accordance with one aspect of the present invention, a study was conducted to develop formulas for expressing body fat percentage in terms of BMI and other potential independent variables such as age and ethnicity. Although the present application describes formulas that were developed from a particular battery of experiments by way of example, it is to be understood that the present invention is not so limited and may be used with results from other experimental configurations.

Accordingly, three groups of experimental subjects were recruited in New York City, USA, Cambridge, UK, and Jekei, Japan. The body fat of the subjects was measured by DXA at all three centers, and, in addition, tritium dilution volume and body density were quantified in the USA and UK sites to the body fat percentage by the 4-Compartment method. Subjects were a convenience sample recruited through advertisements in local newspapers, posted flyers, or through referral for body weight evaluation. The subject pool consisted of 1626 healthy adults, ranging in age, body weight, and ethnicity. In this experiment, three ethnic groups were evaluated: African American at the USA cite, Caucasian at the USA and UK sites, and Asian at the Japan site.

Figure 13:
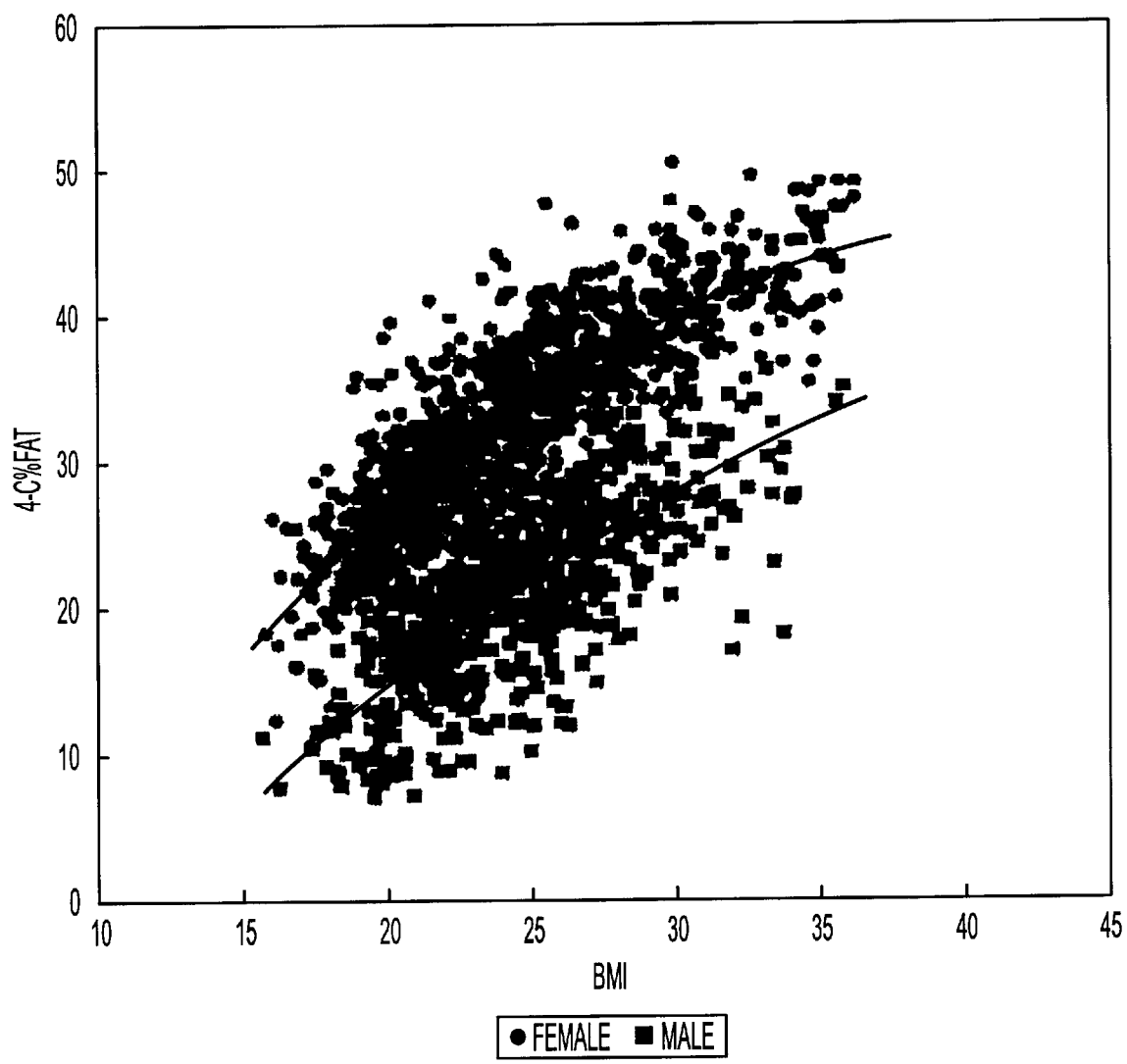
FIG. 13 is a graph of BMI plotted against body fat percentage.

Once passing the screening evaluation, the BMI for the subjects was calculated, and the subjects completed all the available the direct body fat measurements on the same day. FIG. 13 is a graph of the subjects' BMI plotted against the measured body fat percentages of the subjects. Females are marked in the graph with a solid circle and males are indicated by a square. By inspecting the graph, there is a relationship between the body fat percentage and BMI, with the body fat percentage being distributed over a curve for both the males and females.

Figure 14:
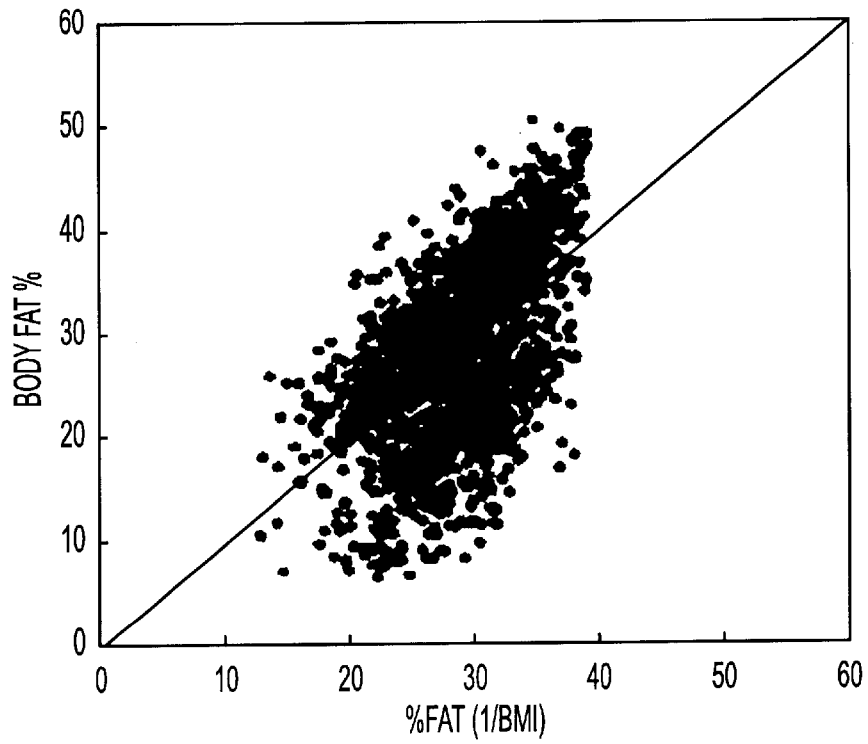
FIG. 14 is a graph of the reciprocal of BMI plotted against body fat percentage.

Next, the reciprocal of the BMI (1/BMI) was plotted against the body fat percentage, which resulted in the graph shown in FIG. 14. A linear relationship between 1/BMI and the body fat percentage was derived by a regression model, which finds a line that minimizes the square of the errors. Therefore, the body fat percentage can be estimated from the reciprocal of the BMI according to the following equation:

$$\text{Body Fat \%} = A - K \times 1/\text{BMI}, \tag{1}$$

where A and K are constants, and BMI is the body mass index. The precise values of the A and K derive from the experiment results and will differ, depending on the experiments that were performed. In this model, the correlation coefficient is 0.576.

Figure 15:
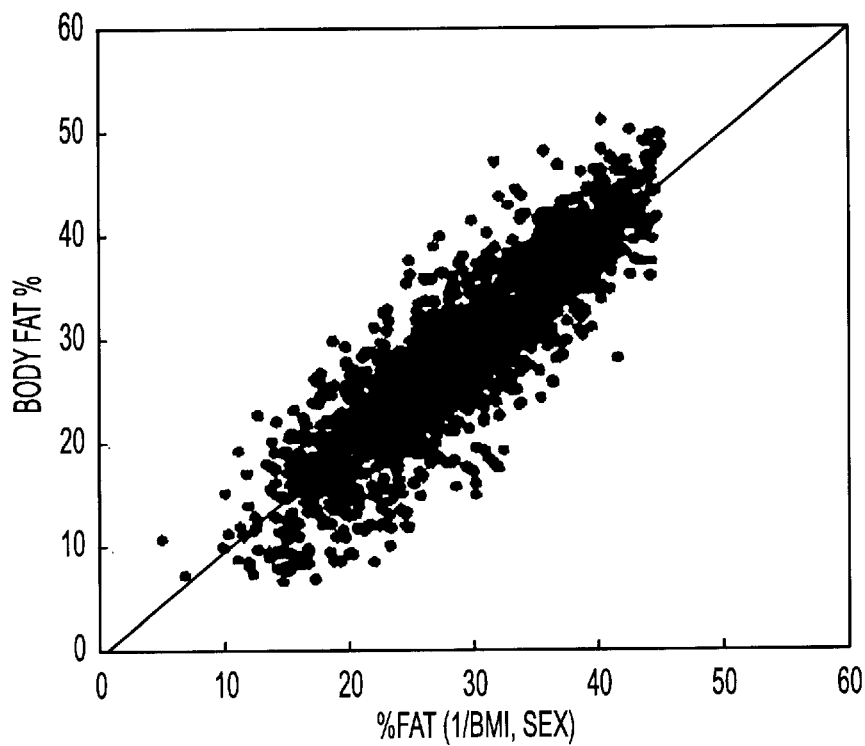
FIG. 15 is a graph of 1/BMI and sex plotted against body fat percentage.

It was observed that, in general, females have a higher body fat percentage than corresponding males. Thus, the correlation in the model of equation (1) can be improved by taking the sex of the subjects into account, using the following equation, for example:

$$\text{Body Fat \%} = -K \times 1/\text{BMI} - B \times \text{sex} + C \times \text{sex} \times 1/\text{BMI}, \tag{2}$$

where A, B, C, and K are constants, "sex" is a variable that indicates the sex of the person (e.g. 0 for females and 1 for males), and BMI is the body mass index of the person. The precise values of A, B, C, and K derive from the experiment results and will differ from implementation to implementation, depending on the experiments that were performed. In this model, a graph of which is illustrated in FIG. 15, the correlation coefficient raises to 0.885.

Figure 16:
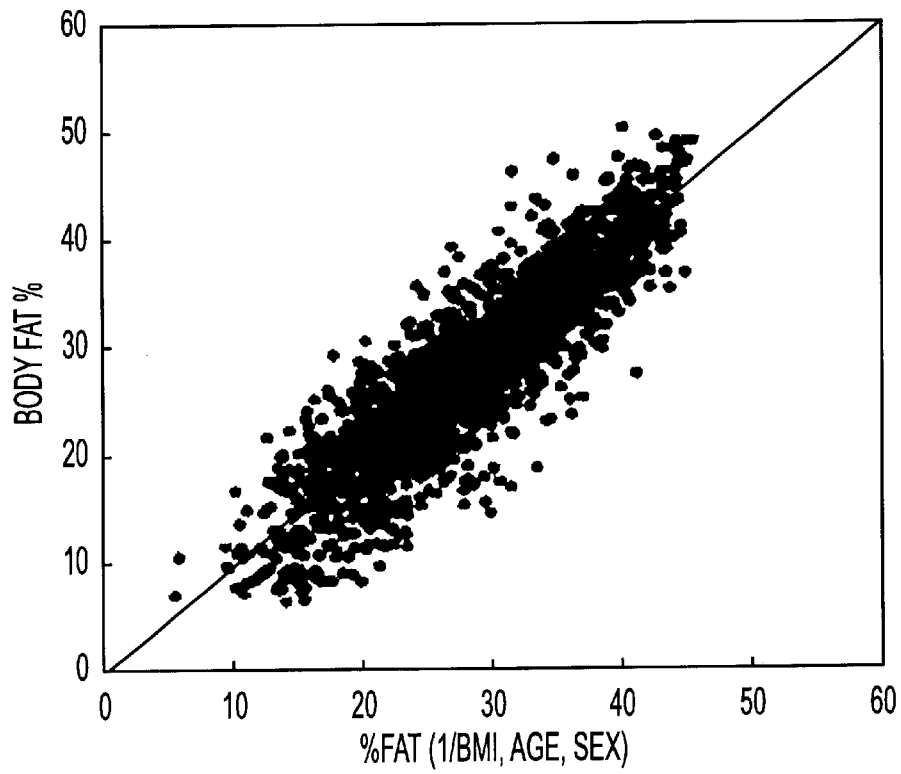
FIG. 16 is a graph of 1/BMI, age, and sex plotted against body fat percentage.

Furthermore, it was found that older subjects tend to have a higher body fat percentage than their younger counterparts. Thus, the correlation can be improved by taking the age of the subjects into account, using the following equation, for example:

$$\text{Body Fat \%} = A - K \times 1/\text{BMI} - B \times \text{age} - C \times \text{sex} + D \times \text{sex} \times \text{age} + E \times \text{sex} \times 1/\text{BMI}, \tag{3}$$

where A, B, C, D, E, and K are constants, "sex" is a variable that indicates the sex of the person (e.g. 0 for females and 1 for males), "age" is a variable that indicates the age of the person, and BMI is the body mass index of the person. The precise values of A, B, C, D, E, and K derive from the experiment results and will differ from implementation to implementation, depending on the experiments that were performed In this model, a graph of which is illustrated in FIG. 16, the correlation coefficient raises to 0.889.

Figure 17:
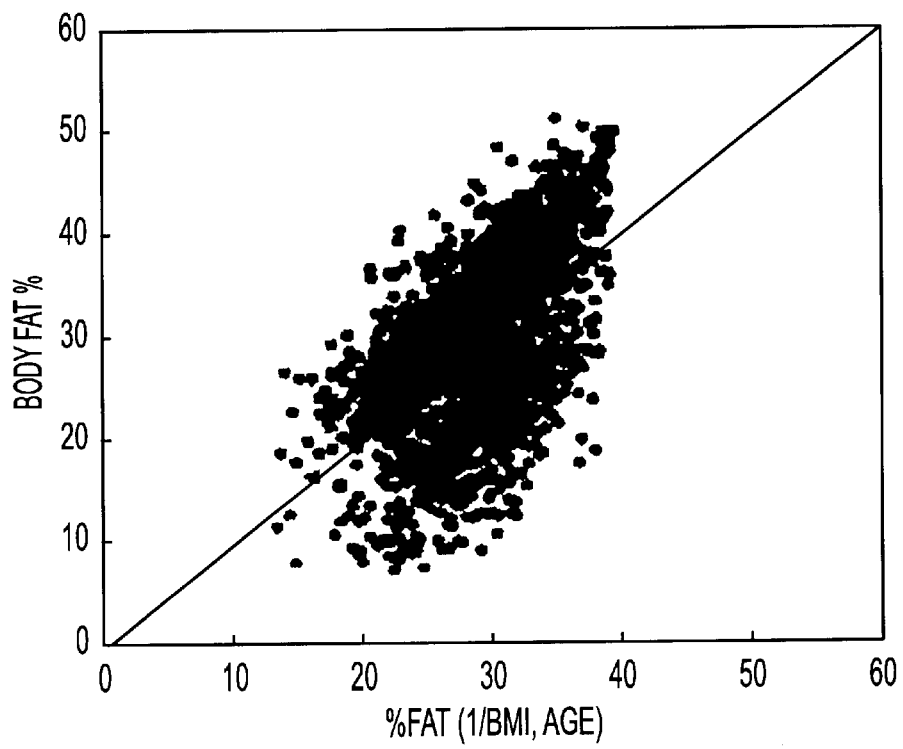
FIG. 17 is a graph of 1/BMI and age plotted against body fat percentage.

If only the age but not the sex of the person was considered, this scenario can be modeled with the following equation:

$$\text{Body Fat \%} = A - K \times 1/\text{BMI} - B \times \text{age}, \quad (4)$$

where A, B, and K are constants, "age" is a variable that indicates the age of the person, and BMI is the body mass index of the person. The precise values of A, B, and K derive from the experiment results and will differ, depending on the experiments that were performed. In this model, a graph of which is illustrated in FIG. 17, the correlation coefficient is 0.576.

Since the sex of the person has a stronger influence on the body fat percentage, it is possible to take sex into account into the age model of equation (4) with two sex-specific regression formulas, one for males and the other for females, rather than employing sex as a variable. In this case, the following equations may be used, in which the corresponding constants A1 vs. A2 and B1 vs. B2 are different:

$$\text{Body Fat \% (male)} = A1 - K1 \times 1/\text{BMI} - B1 \times \text{age}, \quad (5)$$

$$\text{Body Fat \% (female)} = A2 - K2 \times 1/\text{BMI} - B2 \times \text{age}, \quad (6)$$

Figure 18:
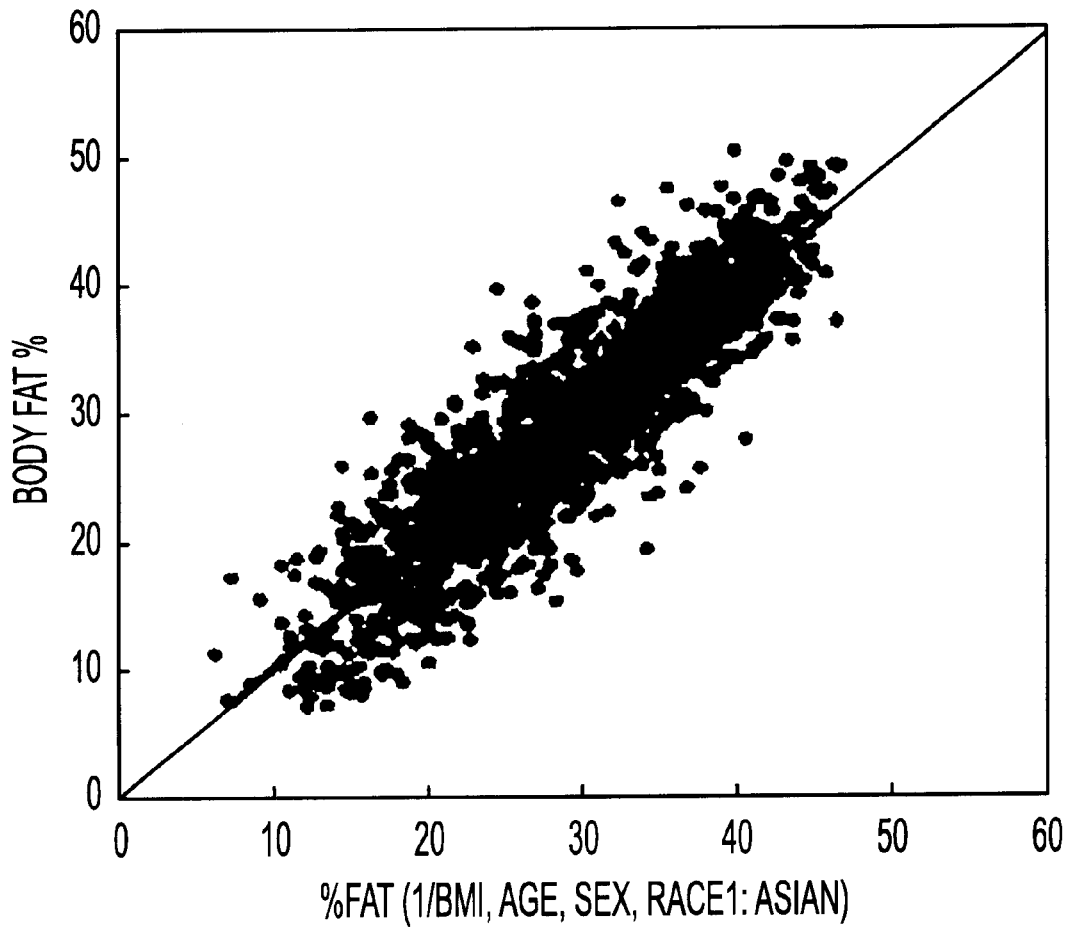
FIG. 18 is a graph of 1/BMI, age, sex, and ethnicity plotted against body fat percentage.

Further improvements in the correlation can be attained by taking the ethnicity of the subjects into account For example, it has been found that Asian tended to have a higher body fat percentage for a given BMI than did African Americans or Caucasians, particularly at the lower age ranges. Thus, the correlation can be improved by taking the ethnicity of the subjects into account, using the following equation, for example:

$$\text{Body Fat \%} = A - K \times 1/\text{BMI} - B \times \text{sex} - C \times \text{age} + D \times \text{asian} \times 1/\text{BMI} + E \times \text{asian} \times \text{age} + F \times \text{sex} \times \text{age} + G \times \text{sex} \times 1/\text{BMI}, \quad (7)$$

where A, B, C, D, E, F, G. and K are constants, "sex" is a variable that indicates the sex of the person (e.g. 0 for females and 1 for males), "age" is a variable that indicates the age of the person, "asian" is a variable that indicates whether the person is belongs to an Asian ethnic group, and BMI is the body mass index of the person. The precise values of A, B, C, D, E, F, G, and K derive from the experiment results and will differ from implementation to implementation, depending on the experiments that were performed. In this model, a graph of which is illustrated in FIG. 18, the correlation coefficient raises to 0.896.

Figure 19:
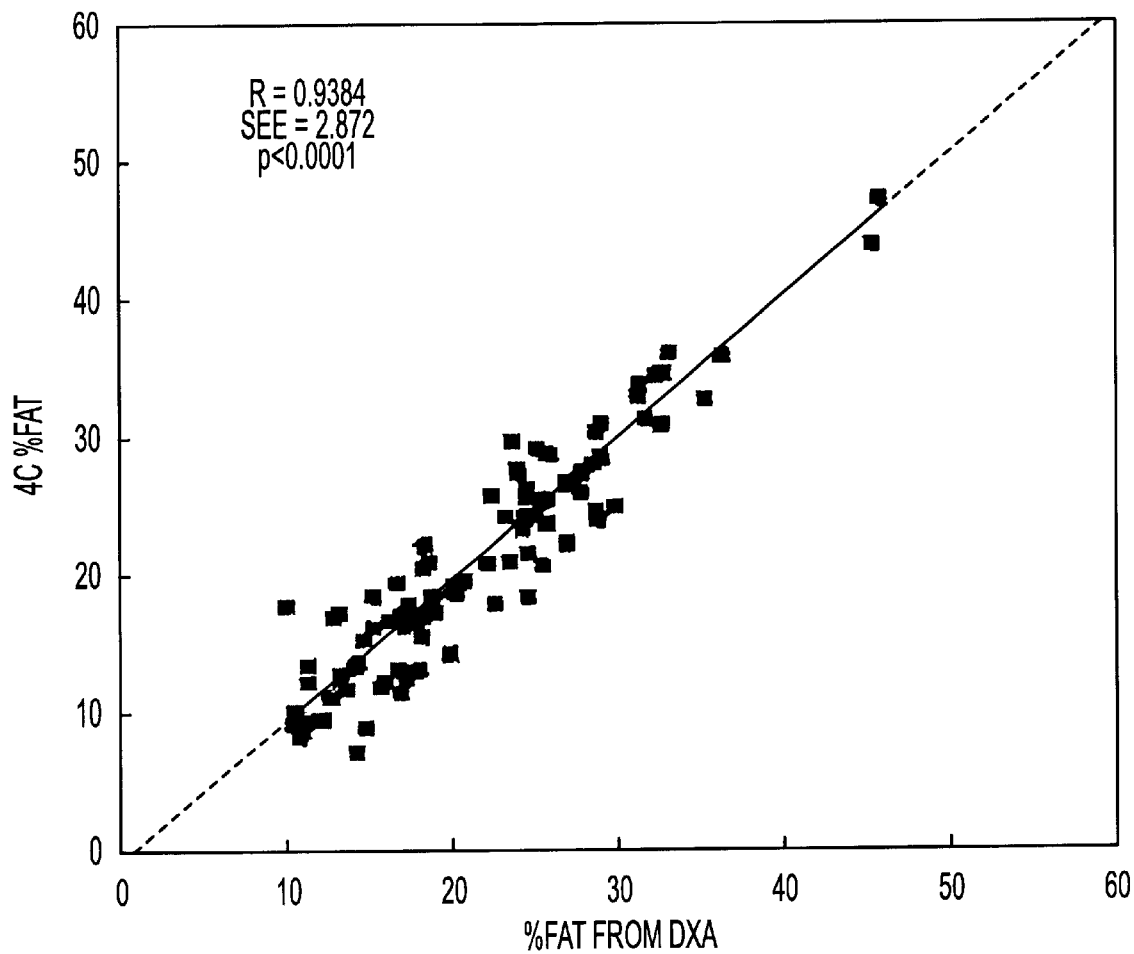
FIG. 19 is a graph of body fat percentage measured by DXA plotted against body fat percentage as determined by the 4-Compartment approach for males.
Figure 20:
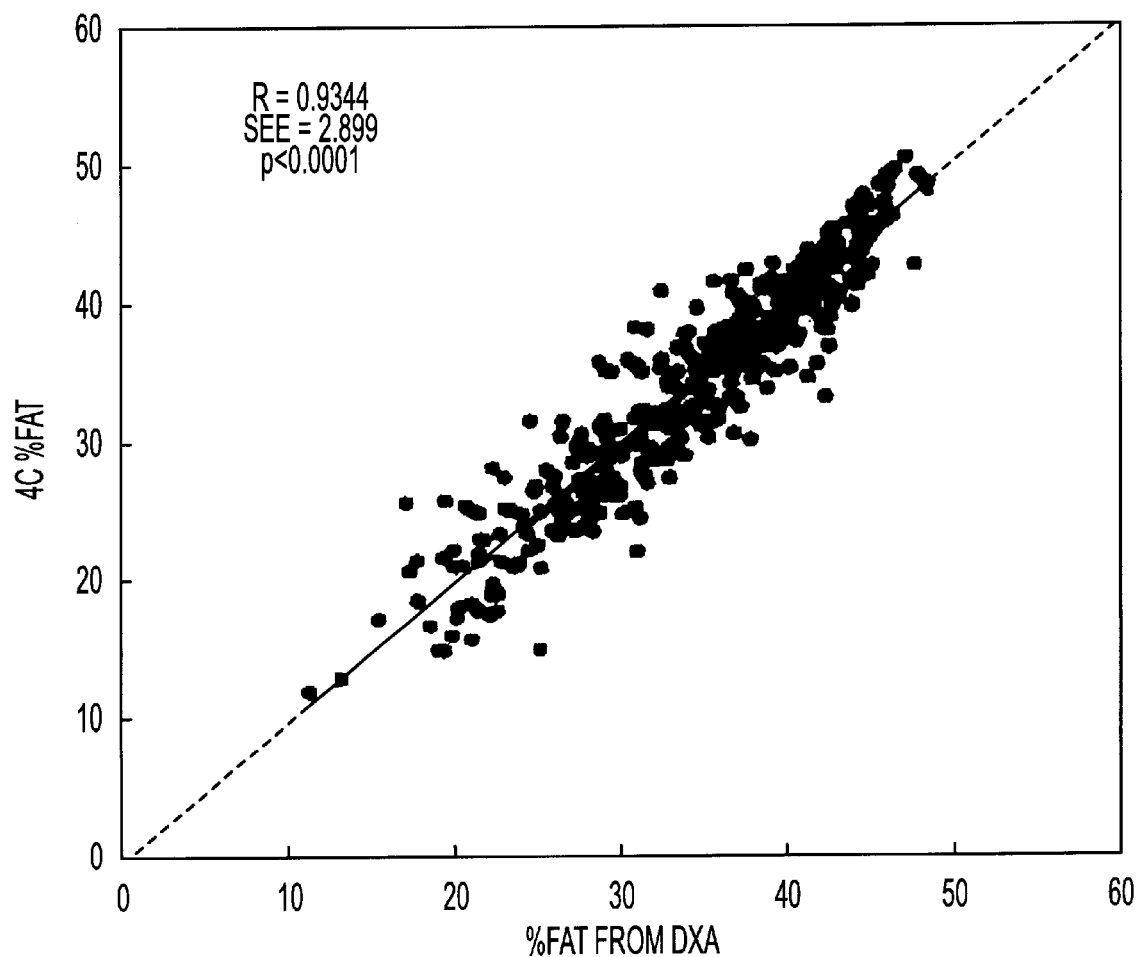
FIG. 20 is a graph of body fat percentage measured by DXA plotted against body fat percentage as determined by the 4-Compartment approach for females.

In the experiment, two measurements of body fat were performed at the USA and UK sites, one based on DXA and the other using a 4-Compartment technique, which uses the measured mineral mass, total body water (which requires drinking heavy water), and body density/volume values for a person These measurements were also regressed in males and females (see FIGS. 19 and 20, respectively) to develop the following equation:

$$4\text{-}C \text{ Body Fat \%} (4\text{-}C) = A - K \times \text{DXA Body Fat \%}, \quad (8)$$

where A and K am constants and "DXA Body Fat %" is the body fat percentage based on the DXA technique is the body mass index of the person. The correlation constant for males in this experiment is 0.9364 and 0.934 for females, showing a high correlation for between the DXA technique and the 4-C approach. The 4-C body fat percentage can be reliably estimated from the DXA body fat percentage, without having the subject drink heavy water.

BODY FAT CALCULATOR

One aspect of the present invention relates to a simple device for estimating the body fat percentage for a person FIG. 1 depicts a body fat calculator 1 in accordance with one embodiment of the present invention, which does not require the use of special or expensive equipment, such as X-ray machines, or exotic chemicals, such as heavy water.

Various components are disposed on the front face of the body fat calculator 1, including a power switch 2, an up key 3, a down key 4, an enter key 5, and a display screen 6. The power switch 2 is provided for turning the body fat calculator 1 on and off. The up key 3 and the down key 4 permit a user to enter data about the user by incrementing or decrementing a display value corresponding to the user's standing height body weight, sex, age, and ethnicity. The display screen 6 can be a liquid crystal display (LCD), or LED display, etc., for displaying numbers and icons to the user in the course of operation.

FIG. 2 is an electrical block diadem of one implementation of the body fat calculator 1. This implementation of the body fat calculator 1 includes a microcontroller (or CPU) 7 that is coupled to the input elements of the body fat calculator 1, including the up key 3, the down key 4, and the enter key 5. The power switch 2 is coupled to the microcontroller 7 and to a power supply 8, which can be a battery disposed within the body fat calculator 1, for switching power on and off to the microcontroller 7. The display screen 6 is also coupled to the microcontroller 7 through a display driver (not shown).

FIG. 3 is a flowchart, illustrating the operation of using the body fat calculator 1 in accordance with one embodiment of the present invention. When a user begins to use the body fat calculator 1, the user presses the power switch 2, which connects the power source 8 to the microcontroller 7. Upon application of power, the microcontroller 7 undergoes an initialization sequence (step 1), which sets up the display screen 6 to display an initial display screen. By way of example, one initial display screen is shown in FIG. 4(a), but it is to be understood that the present invention is not so limited and various screens may be shown.

In the illustrated embodiment, by way of example, the initial display screen 400 includes areas for indicating the sex, age, height, weight, and ethnicity of the user. In other embodiments, additional and/or fewer areas for corresponding variables may be employed. In the initial display screen, default values for the age (25 years), height (170 cm), weight (55 kg) are displayed, and all supported values of sex (male or female) and ethnicity (Asian, black, white) arc shown. Areas are also reserved for outputting the BMI, body fat percentage, and body fat mass, but these values are displayed later after being calculated.

At step 2, the user presses the up key 3 to indicate that he is a male or the down key 4 to indicate that she is a female. In response, only the corresponding icon is displayed (with the other icon being turned off). For example, if the user pressed the down key 4 to indicate that she is female, then the female icon is displayed and the male icon is turned off, as illustrated in screen 402 of FIG. 4(b). Upon reaching the desired value for sex, the user presses the enter key 5, which is tested at step 3, and execution proceeds to step 4.

At step 4, the user repeatedly presses the up key 3 or the down key 4 to add one or subtract one, respectively, from the displayed age, until the desired age is reached. In the example, illustrated as screen 404 in FIG. 4(c), the age has been incremented to 27 years. Upon reaching the desired age, the user presses the enter key 5, which is tested at step 5, and execution proceeds to step 6.

At step 6, the user repeatedly presses the up key 3 or the down key 4 to add a predetermined amount (such as 5 cm) or subtract the predetermined amount, respectively, from the displayed height, until the desired height is reached. In the example, illustrated as screen 406 in FIG. 4(*d*), the height has been decremented to 165 cm. Upon reaching the desired height, the user presses the enter key 5, which is tested at step 7, and execution proceeds to step 8. Although metric units are depicted in this example, U.S. customary units such as inches may also be employed.

At step 8, the user repeatedly presses the up key 3 or the down key 4 to add a predetermined amount (such as 1 kg) or subtract the predetermined amount, respectively, from the displayed weight, until the desired height is reached. In the example, illustrated as screen 408 in FIG. 4(*e*), the weight has been changed to 53 kg Upon reaching the desired weight, the user presses the enter key 5, which is tested at step 9, and execution proceeds to step 10. Although metric units are depicted in this example, U.S. customary units such as pounds may also be employed.

At step 10, the user repeatedly presses the up key 3 or the down key 4 to select one of the supported ethnicities. In the example, illustrated as screen 410 in FIG. 4(*f*), the user has selected the Asian ethnicity and presses the enter key 5, which is tested at step 11 for continuation to step 12.

At step 12, the information that was received from the user is used to calculate the BMI, body fat percentage, and body fat mass. In this implementation the BMI is calculated as the weight/height$^2$, and the body fat percentage is calculated using equation (7) explained herein above. The body fat miss is calculated as the product of the body fat percentage and the weight This information is displayed on the display screen 6, as illustrated in the output display screen 412 of FIG. 4(*g*). After a preset period of time, for example 30 seconds, as determined by an internal timer of microcontroller 7, the body fat controller 1 automatically shuts itself off to conserve power.

BODY FAT CALCULATOR SCALE

Figure 5:
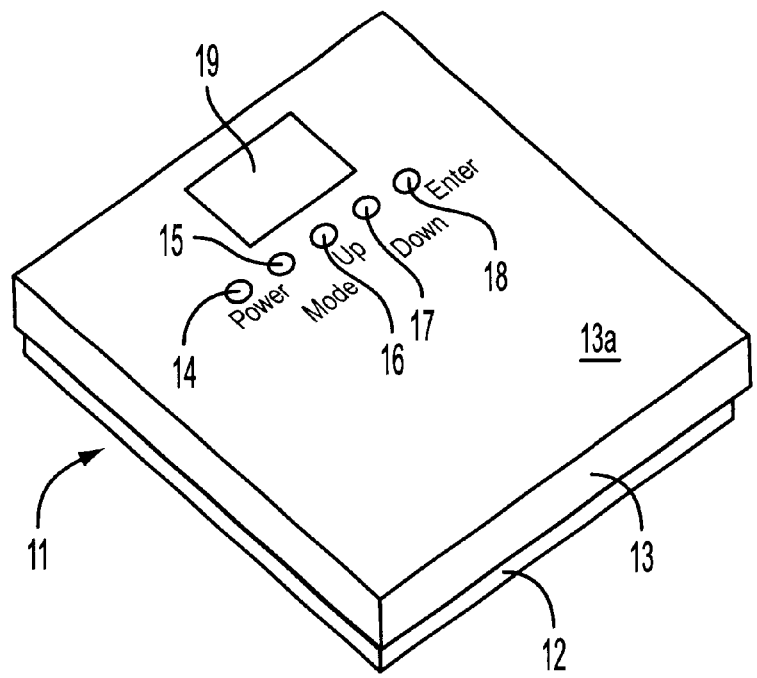
FIG. 5 depicts a scale in accordance with one embodiment of the present invention.

One embodiment of the present invention is a scale that can estimate the body fat percentage of a person. Referring to FIG. 5, a scale 11 comprises an under body 12 and an upper body 13. Disposed on the top face 13A of the upper body 13 include a power switch 14, a mode key 15, an up key 16, a down key 17, an enter key 18, and a display screen 19. The power switch 15 is provided to turn the scale 11 on and off. The mode key 15, the up key 16 and the down key 17 permit a user to enter data about the user such as the user's standing height, sex, age, and ethnicity. The display screen 19 can be a liquid crystal display (LCD), or LED display, etc., for displaying numbers and icons to the user in the course of operation.

Figure 6:
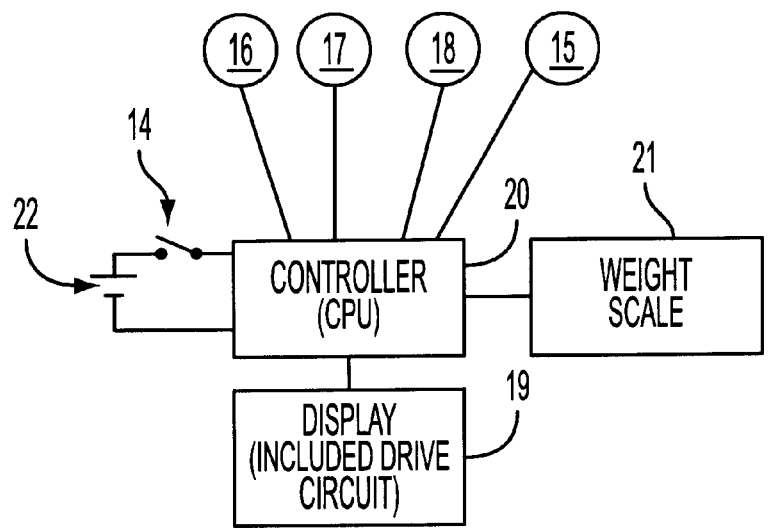
FIG. 6 depicts an electrical block diagram of the scale depicted in FIG. 5.

FIG. 6 is an electrical block diagram of one implementation of the scale 11. This implementation of the scale 11 includes a microcontroller (or CPU) 20 that is coupled to the input elements of the scale 11, including mode key 15, the up key 16 and the down key 17. The power switch 14 is coupled to the microcontroller 20 and to a power supply 22, which can be a battery disposed within the scale 11, for switching power on and off to the microcontroller 20. The display screen 19 is also coupled to the microcontroller 20 through a display driver (not shown). Furthermore, the microcontroller 20 is coupled to an electronic weight scale 21, which is configured for providing weight information to the microcontroller 20 when a person is standing on the upper body 12.

Figure 7:
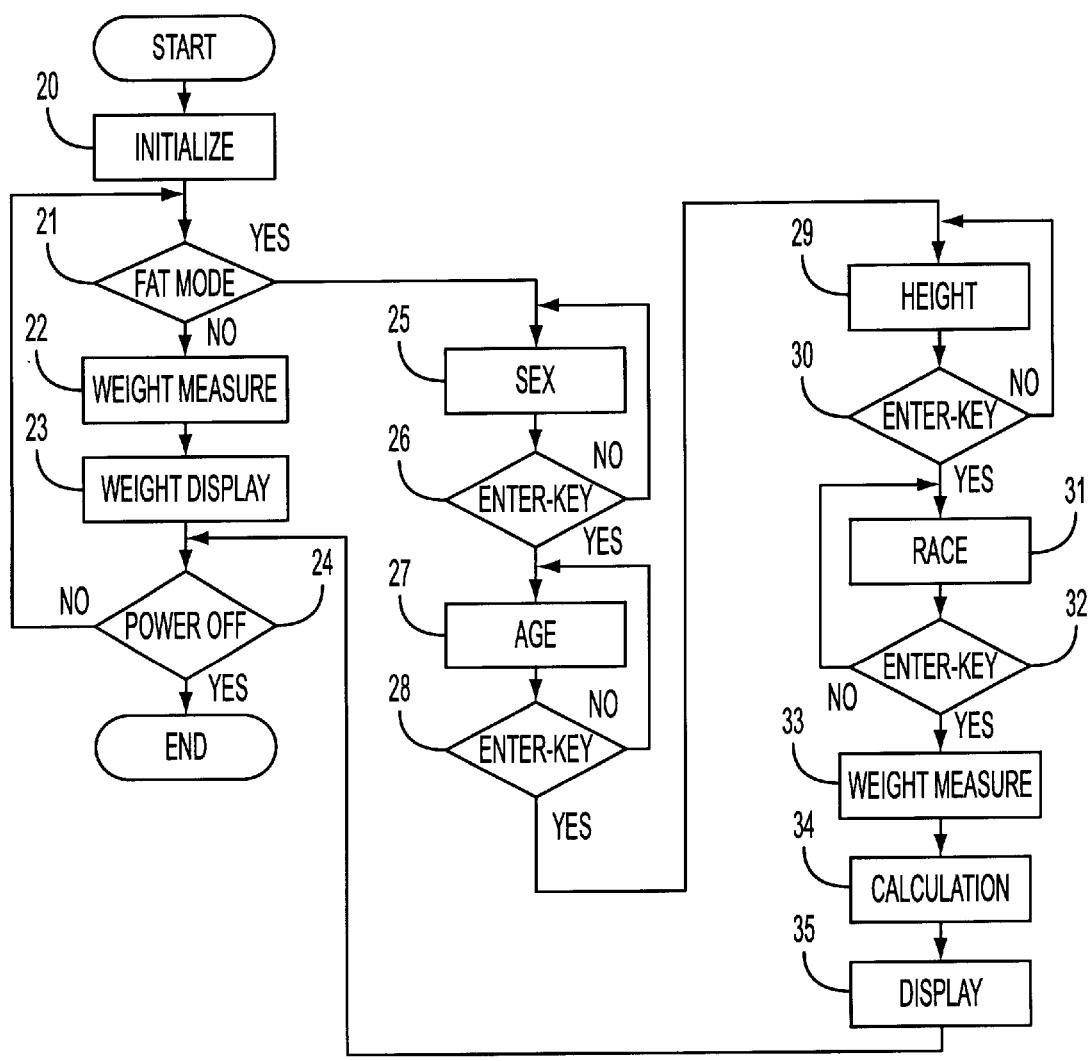
FIG. 7 is a flowchart illustrating the operation using the scale depicted in FIG. 5.

FIG. 7 is a flowchart, illustrating the operation of using the scale 11 in accordance with one embodiment of the present invention. When a user begins to use the scale 1 1, the user presses the power switch 14, which connects the power source 22 to the microcontroller 20. Upon application of power, the microcontroller 20 undergoes an initialization sequence (step 20), which initialization the scale 11.

Figure 8:
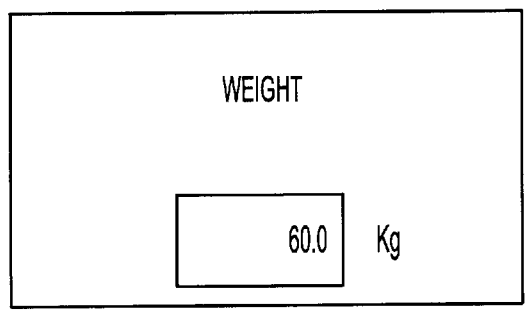
FIG. 8 depicts a screen displayed in one mode by the scale depicted in FIG. 5.

At step 21, the microcontroller 20 check to determined if the user has presses the fat mode button 15. If the user has not pushed the fat mode button 15, the scale 11 then measures the person's weight using the weight scale 21 (step 22) and displays the result in a display screen shown in FIG. 8 (step 23), in which, for example, the user weights 60 kg (about 132 lbs). After 30 seconds, tested in step 24, the microcontroller 20 shuts the scale 11 off to converse power.

If, on the other hand, the fat mode button 15, was pressed, then the microcontroller 20 sets up the display screen 19 to display an initial fat display screen 900. By way of example, one initial display screen 900 is shown in FIG. 9(*a*), but it is to be understood that the present invention is not so limited and various screens may be shown.

In the illustrated embodiment, by way of example, the initial fat display screen 900 includes areas for indicating the sex, age, height, weight, and ethnicity of the user. In other embodiments, additional and/or fewer areas for corresponding variables may be employed. In the initial display screen, default values for the age (25 years), height (170 cm), weight (55 kg) are displayed, and all supported values of sex (male or female) and ethnicity (Asian, black, white) are shown. Areas are also reserved for outputting the BMI, body fat percentage, and body fat mass, but these values are displayed later after being calculated.

At step 25, the user presses the up key 16 to indicate that he is a male or the down key 17 to indicate that she is a female. In response, only the corresponding icon is displayed (with the other icon being turned off). For example, if the user pressed the down key 17 to indicate flat she is female, then the female icon is displayed and the male icon is turned off, as illustrated in screen 902 of FIG. 9(*b*). Upon reaching the desired value for sex, the user presses the enter key 18, which is tested at step 26, and execution proceeds to step 27.

At step 27, the user repeatedly presses the up key 16 or the down key 17 to add one or subtract one, respectively, from the displayed age, until the desired age is reached. In the example, illustrated as screen 904 in FIG. 9(*c*), the age has been incremented to 27 years. Upon reaching the desired age, the user presses the enter key 18, which is tested at step 28, and execution proceeds to step 29.

At step 29, the user repeatedly presses the up key 16 or the down key 17 to add a predetermined amount (such as 5 cm) or subtract the predetermined amount, respectively, from the displayed height, until the desired height is reached. In the example, illustrated as screen 906 in FIG. 9(*d*), the height has been decremented to 165 cm. Upon reaching the desired height, the user presses the enter key 18, which is tested at step 30, and execution proceeds to step 31. Although metric units are depicted in this example, U.S. customary units such as inches may also be employed.

At step 31, the user repeatedly presses the up key 16 or the down key 17 to select one of the supported ethnicities. In the example, illustrated as screen 908 in FIG. 9(*e*), the user has selected the Asian ethnicity and presses the enter key 18, which is tested at step 32 for continuation to step 33. At step 33, the scale 11 then measures the person's weight using the weight scale 21. The result is then displayed (step 34) in screen 91 shown in FIG. 9(f), in which the user weights 53 kg. Although metric units are depicted in this example, U.S. customary units such as pounds may also be employed.

At step 34, the information that was received from the user is used to calculate the BMI, body fat percentage, and body fat mass. In this implementation, the BMI is calculated as the weight/height$^2$, and the body fat percentage is calculated using equation (7) explained herein above. The body fat mss is calculated as the product of the body fat percentage and the weight This information is displayed on the display screen 6, as illustrated in the output display screen 912 of FIG. 49(g). After a preset period of time, for example 30 seconds, as determined by an internal timer of microcontroller 20 in step 24, the scale 11 automatically shuts itself off to conserve power.

BODY FAT ESTIMATION OVER A NETWORK

Figure 10:
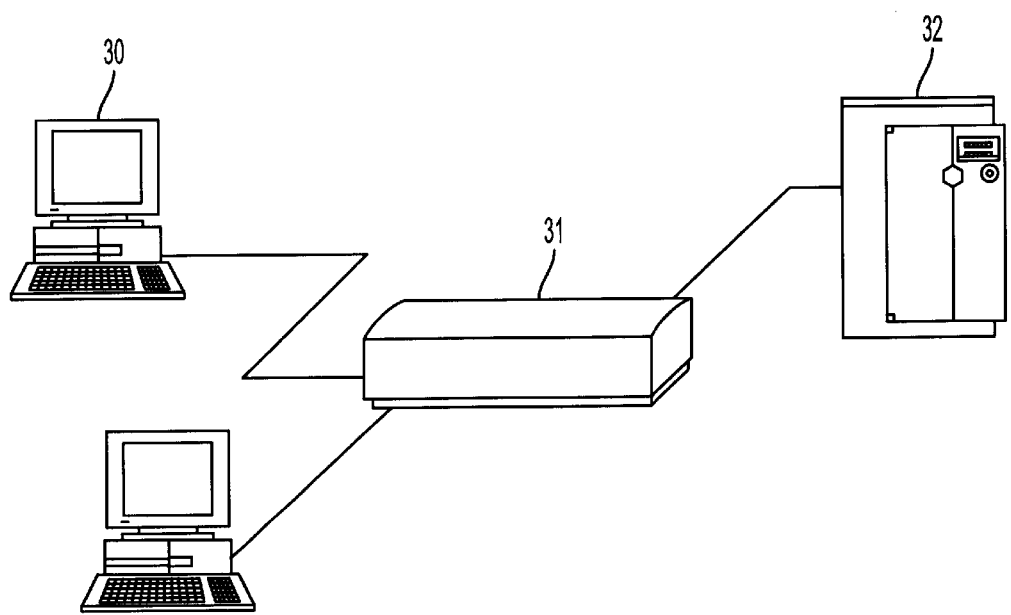
FIG. 10 is a diagram of a computer network that can be used to implement one embodiment of the present invention.

Another embodiment of the present invention related to performing body fat estimation over a network, such as a local area network (LAN), a wide-area network (WAN), or the Internet. FIG. 10 depicts a computer network in which a personal computers 20 is coupled, via a hub 31, to a server 32 In this arrangement, a user at personal computer 30 desires to obtain the user's body fat percentage based on simple variables by interacting with server 32 over a computer network.

Figure 11:
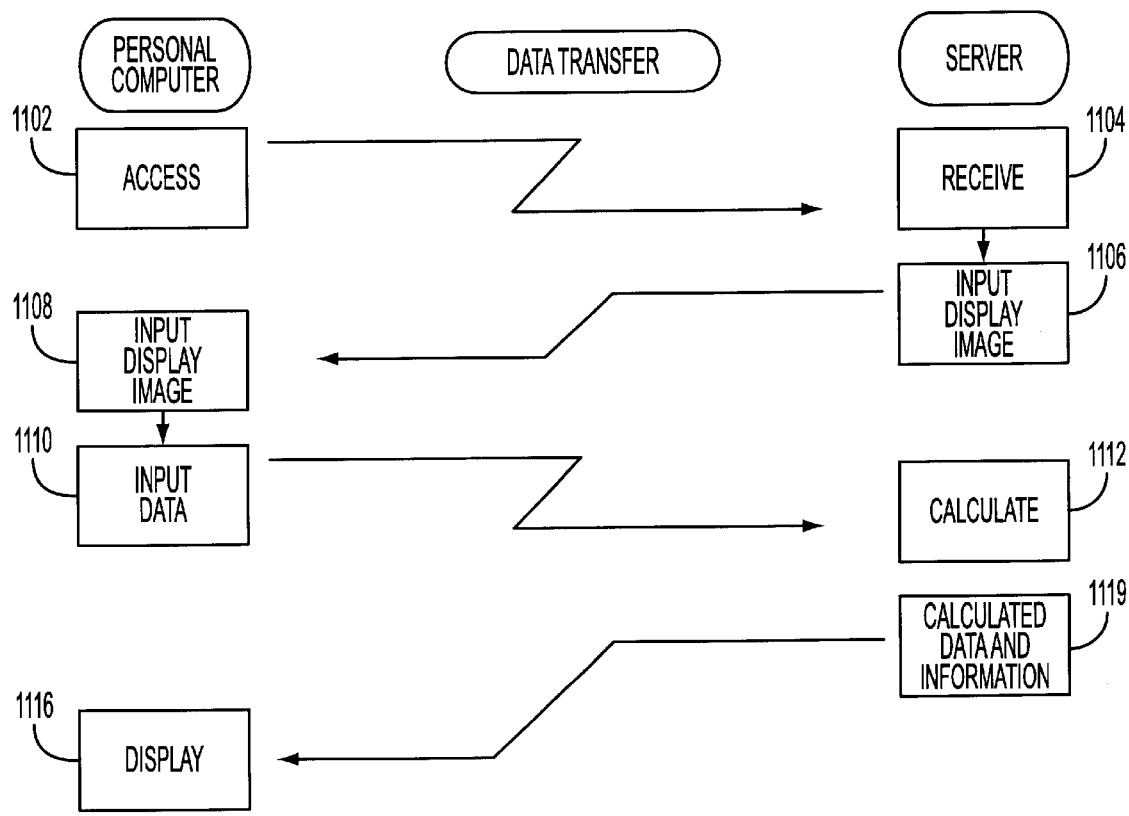
FIG. 11 is a flowchart illustrating the operation using the computer network depicted in FIG. 10.

FIG. 11 illustrates the operation of this embodiment, in which the user obtains access to personal computer 30 (for example by login and password procedures) and then to server 32, for example, by accessing a web site maintained at server 32 (step 1102). When the server 32 received a request for the web site, typical via a hypertext transfer protocol (HTTP) GET command with a URL designating the address of the web site. The server 32 receives the request (step 1104), fetches web page or other generates an input display image (step 1106) and transmits the web page to the personal computer 30.

In response, the person computer receives and displays the web page (step 1108), which typically includes a form for inputting data. At step 1110, the user enters the requested data, such as sex, age, height, weight, and ethnicity (or even BMI directly), and transfers the entered information to the server 32, for example, by an HTTP POST command. In response, the server 32 receives the information, and makes the appropriate calculations to determine, inter alia, the body fat percentage based on at least some of the input variables, for example, by applying the above-explained regression equations (step 1112). The calculation results are then assembled into an output web page (step 1141 and transmitted to the user's personal computer 30 and displayed (step 1116).

HARDWARE OVERVIEW

Figure 12:
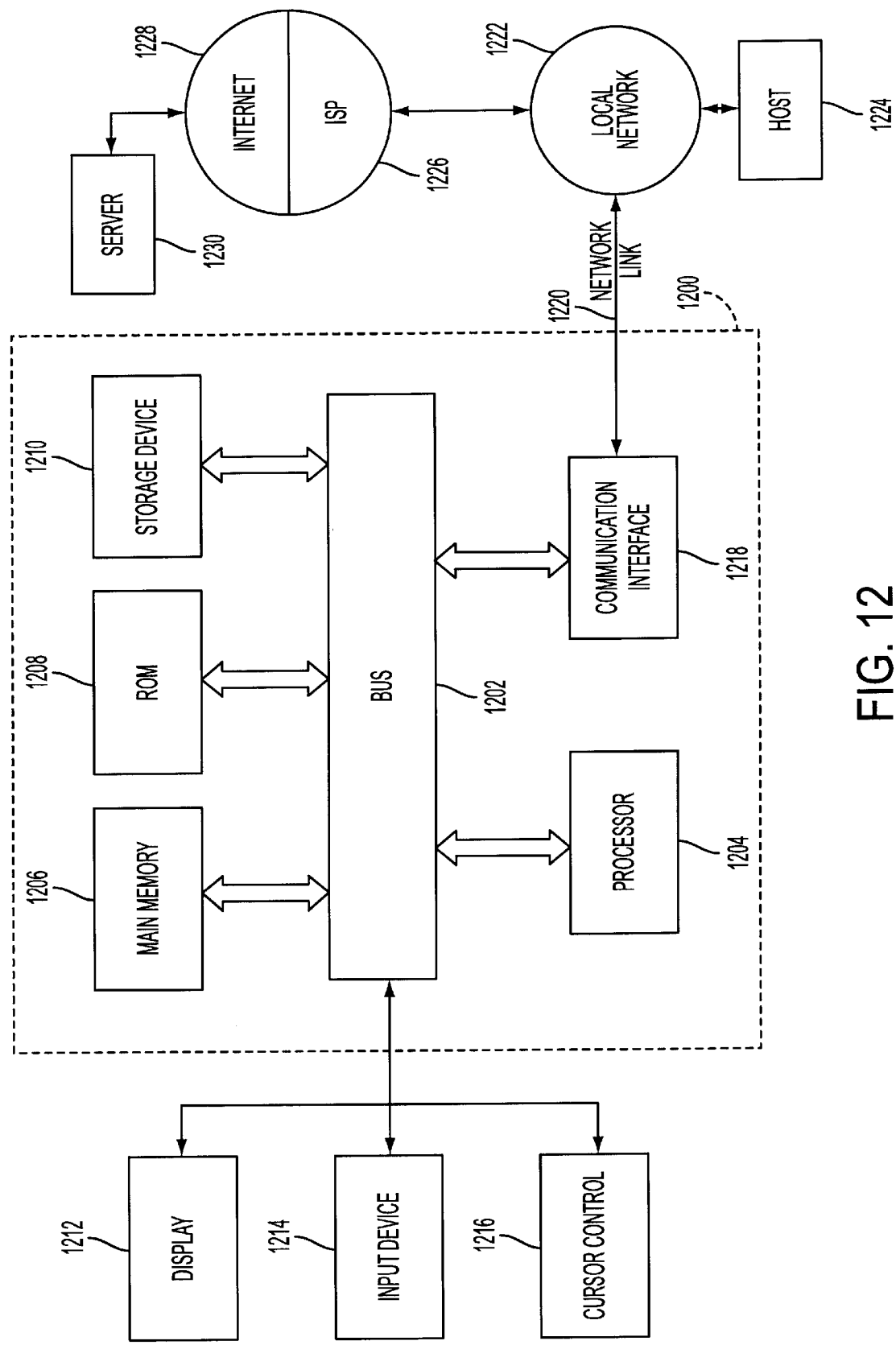
FIG. 12 is a diagram that depicts a computer system that can be used to implement one embodiment of the present invention.

FIG. 12 is a block diagram that illustrates a computer system 1200, such as personal computer 30, upon which an embodiment of the invention may be implemented. Computer system 1200 includes a bus 1202 or other communication mechanism for communicating information, and a processor 1204 coupled with bus 1202 for processing information. Computer system 1200 also includes a main memory 1206, such as a random access memory (RAM) or other dynamic storage device, coupled to bus 1202 for storing information and instructions to be executed by processor 1204. Main memory 1206 also may be used for storing temporary variables or other intermediate information during execution of instructions to be executed by processor 1204. Computer system 1200 further includes a read only memory (ROM) 1208 or other static storage device coupled to bus 1202 for storing static information and instructions for processor 1204. A storage device 1210, such as a magnetic disk or optical disk, is provided and coupled to bus 1202 for storing information and instructions.

Computer system 1200 may be coupled via bus 1202 to a display 1212, such as a cathode ray tube (CTR), for displaying information to a computer user. An input device 1214, including alphanumeric and other keys, is coupled to bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The invention is related to the use of computer system 1200 for estimating body fat percentage. According to one embodiment of the invention, estimating body fat percentage is provided by computer system 1200 in response to processor 1204 executing one or more sequences of one or more instructions contained in main memory 1206. Such instructions may be read into main memory 1206 from another computer-readable medium, such as storage device 1210. Execution of the sequences of instructions contained in main memory 1206 causes processor 1204 to perform the process steps described herein. One or more processors in a multi-processing arrangement may also be employed to execute the sequences of instructions contained in main memory 1206. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 1204 for execution. Such a medium may take many forms, including but not limited to, non-volatile media, volatile media, and transmission media. Non-volatile media include, for example, optical or magnetic disks, such as storage device 1210. Volatile media include dynamic memory, such as main memory 1206. Transmission media include coaxial cables, copper wire and fiber optics, including the wires that comprise bus 1202 Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM any other memory chip or cartridge, a carrier wave as described hereinafter, or any other medium from which a computer can read.

Various forms of computer readable media may be involved in carrying one or more sequences of one or more instructions to processor 1204 for execution For example, the instructions may initially be borne on a magnetic disk of a remote computer. The remote computer can load the instructions into its dynamic memory and send the instructions over a telephone line using a modem. A modem local to computer system 1200 can receive the data on the telephone line and use an e d transmitter to convert the data to an infrared signal. An infrared detector coupled to bus 1202 can receive the data carried in the infrared signal and place the data on bus 1202. Bus 1202 carries the data to main memory 1206, from which processor 1204 retrieves and executes the instructions. The instructions received by main memory 1206 may optionally be stored on storage device 1210 either before or after execution by processor 1204.

Computer system 1200 also includes a communication interface 1218 coupled to bus 1202. Communication interface 1218 provides a two-way data communication coupling to a network link 1220 that is connected to a local network 1222. For example, communication interface 1218 may be an integrated services digital network (ISDN) card or a modem to provide a data communication connection to a corresponding type of telephone line. As another example, communication interface 1218 may be a local area network (LAN) card to provide a data communication connection to a compatible LAN. Wireless links may also be implemented In any such implementation, communication interface 1218 sends and receives electrical, electromagnetic or optical signals that carry digital data streams representing various types of information.

Network link 1220 typically provides data communication through one or more networks to other data devices. For example, network link 1220 may provide a connection through local network 1222 to a host computer 1224 or to data equipment operated by an Internet Service Provider (ISP) 1226. ISP 1226 in turn provides data communication services through the worldwide packet data communication network, now commonly refereed to as the "Internet" 1228. Local network 1222 and Internet 1228 both use electrical, electromagnetic or optical signals that carry digital data streams. The signals through the various networks and the signals on network link 1220 and through communication interface 1218, which carry the digital data to and from computer system 1200, are exemplary forms of carrier waves transporting the information.

Computer system 1200 can send messages and receive data, including program code, through the network(s), network link 1220, and communication interface 1218. In the Internet examples a server 130 might transmit a requested code for an application program through Internet 1228, ISP 1226, local network 1222 and communication interface 1218. In accordance with the invention, one such downloaded application provides for estimating body fat percentage as described herein. The received code may be executed by processor 1204 as it is received, and/or stored in storage device 1210, or other non-volatile storage for later execution. In this manner, computer system 1200 may obtain application code in the form of a carrier wave.

While this invention has been described in connection with what is presently considered to be the most practical and preferred embodiment, it is to be understood that the invention is not limited to the disclosed embodiment, but on the contrary, is intended to cover various modifications and equivalent arrangements included within the spirit and scope of the appended clams.

What is claimed is:

1. A machine-implemented method for estimating a body fat percentage of a person, comprising the steps of:
    receiving input indicating data concerning the person;
    estimating the body fat percentage of the person based on a reciprocal of a body mass index (BMI), wherein the body mass index includes a quotient of a weight of the person over a square of a height of the person; and
    outputting the estimated body fat percentage.

2. The method according to claim 1, wherein the data concerning the person comprises an indication of the body mass index of the person.

3. The method according to claim 1, wherein the data concerning the person comprises indications of the weight of the person and the height of the person.

4. The method according to claim 1, wherein the step of said estimating includes the step of:
    calculating the estimated body fat percentage in accordance with an expression comprising $A-K\times 1/BMI$,
    wherein A and K are predetermined constants, and $1/BMI$ is the reciprocal of the body mass index.

5. The method according to claim 1, further comprising the step of receiving input indicating a sex of the person,
    wherein the step of said estimating includes the step of estimating the body fat percentage based on the reciprocal of the body mass index and the sex of the person.

6. The method according to claim 5, wherein the step of said estimating the body fat percentage based on the reciprocal of the body mass index and the sex of the person includes the step of:
    calculating the estimated body fat percentage in accordance with an expression containing $A-K\times 1/BMI-B\times sex+C\times sex\times 1/BMI$,
    wherein A, B, C, and K are predetermined constants, sex indicates the sex of the person, and $1/BMI$ is the reciprocal of the body mass index.

7. The method according to claim 5, further comprising the step of receiving input indicating an age of the person,
    wherein the step of said estimating includes the step of estimating the body fat percentage based on the reciprocal of the body mass index, the sex of the person, and the age of the person.

8. The method according to claim 7, wherein the step of said estimating the body fat percentage based on the reciprocal of the body mass index, the sex of the person, and the age of the person includes the step of:
    calculating the estimated body fat percentage in accordance with an expression containing $A-K\times 1/BMI-B\times age+C\times sex+D\times sex\times age+E\times sex\times 1/BMI$,
    wherein A, B, C, D, E, and K are predetermined constants, sex indicates the sex of the person, age indicates the age of the person, and $1/BMI$ is the reciprocal of the body mass index.

9. The method according to claim 1, farther comprising the step of receiving input indicating an age of the person,
    wherein the step of said estimating includes the step of estimating the body fat percentage based on the reciprocal of the body mass index and the age of the person.

10. The method according to claim 9, wherein the step of said estimating the body fat percentage based on the reciprocal of the body mass index and the age of the person includes the step of:
    calculating the estimated body fat percentage in accordance with an expression containing $A-K\times 1/BMI-B\times age$,
    wherein A, B, and K are predetermined constants, age indicates the age of the person, and $1/BMI$ is the reciprocal of the body mass index.

11. The method according to claim 9, further comprising the step of receiving input indicating a sex of the person,
    wherein the step of said estimating the body fat percentage based on the reciprocal of the body mass index and the age of the person includes the steps of:
    calculating the estimated body fat percentage in accordance with an expression containing $A1-K\times 1/BMI-B1\times age$ if the sex is male, calculating the estimated body fat percentage in accordance with an expression containing A2−K2×1/BMI−B2×age if the sex is female, wherein A1, B1, A2, B2, K1 and K2 are predetermined constants, age indicates the age of the person, 1/BMI is the reciprocal of the body mass index, A1 is different from A2, and B1 is different from B2.

12. The method according to claim 1, for comprising the step of receiving input indicating a sex, an age, and an ethnic group of the person, wherein the step of said estimating includes the step of estimating the body fat percentage based on the reciprocal of the body mass index, the sex of the person, the age of the person, and the ethic group of the person.

13. The method according to claim 12, the step of said estimating the body fat percentage based on the reciprocal of the body mass index, the sex of the person, the age of the person, and the ethnic group of the person includes the step of:

calculating the estimated body fat percentage in accordance with an expression containing A−K×1/BMI−B×sex+C×age+D×asian×1/BMI+E×asian+F×sex×age+G×sex×1/BMI wherein A, B, C, D, E, F, and K are predetermined constants, age indicates the age of the person, asian indicates whether the person belongs to an Asian ethnic group, and 1/BMI is the reciprocal of the body mass index.

14. A machine-implemented method for estimating a body fat percentage of a person, comprising the steps of:

receiving input indicating a body fat percentage measured by dual-energy x-ray absorptiometry (DXA);

estimating a 4-Compartment body fat percentage of the person based on the body fat percentage measured by DXA; and outputting the estimated 4-Compartment body fat percentage.

15. The method according to claim 14, wherein the step of said estimating includes the step of:

calculating the estimated 4-Compartment body fat percentage in accordance with an expression comprising A−K×dxa, wherein A and K are predetermined constants, and dxa is a variable that indicates the body fat percentage measured by DXA.

16. An apparatus for estimating a body fat percentage of a person, comprising:

one or more inputs for receiving data concerning the person;

a controller for estimating the body fat percentage of the person based on a reciprocal of a body mass index (BMI), wherein the body mass index includes a quotient of a weight of the person over a square of a height of the person; and a display for outputting the estimated body fat percentage.

17. A scale for estimating a body fat percentage of a person, comprising:

one or more inputs for receiving data concerning the person;

a weight scale for measuring a weight of the person;

a controller for estimating the body fat percentage of the person based on a reciprocal of a body mass index (BMI), wherein the body mass index includes a quotient of the weight of the person over a square of a height of the person; and a display for outputting the estimated body fat percentage.

18. The scale according to claim 17, wherein:

the data include a mode input; and the controller is configured for selectively displaying one of the estimated body fat percentage and the weight of the person in response to the mode input.

19. A computer-readable medium bearing instructions for estimating a body fat percentage of a person, said instructions being arranged to cause one or more processors upon execution thereby to perform the steps of:

receiving input indicating data concerning the person;

estimating the body fat percentage of the person based on a reciprocal of a body mass index (BMI), wherein the body mass index includes a quotient of a weight of the person over a square of a height of the person; and outputting the estimated body fat percentage.

20. A machine-implemented method for estimating a body fat percentage of a person, comprising the steps of:

inputting data concerning the person at a terminal;

transmitting the data to the server via a network;

estimating the body fat percentage of the person at a server based on a reciprocal of a body mass index (BMI), wherein the body mass index includes a quotient of a weight of the person over a square of a height of the person;

transmitting the estimated body fat percentage to the terminal via the network; and displaying the estimated body fat percentage at the terminal.

21. The method of claim 20, comprising the steps of transmitting a form for inputting the data from the server to the terminal, and displaying the form at the terminal.

22. The method of claim 20, comprising transmitting the data and the body fat percentage over a local area network.

23. The method of claim 20, comprising transmitting the data and the body fat percentage over a wide area network.

24. The method of claim 20, comprising transmitting the data and the body fat percentage over the internet.

25. An apparatus for estimating a body fat percentage of a person, comprising:

a computer terminal for inputting data concerning the person;

a server for estimating the body fat percentage of the person based on a reciprocal of a body mass index (BMI), wherein the body mass index includes a quotient of a weight of the person over a square of a height of the person; and a network connecting the terminal and the server for transmitting the data from the terminal to the server and for transmitting the estimated body fat percentage to the terminal; wherein the terminal comprises a display for displaying the estimated body fat percentage.

26. The apparatus of claim 25, wherein the network comprises a local area network.

27. The apparatus of claim 25, wherein the network comprises a wide area network.

28. The apparatus of claim 25, wherein the network comprises the internet.

29. The apparatus of claim 25, wherein the terminal comprises a personal computer.

30. The apparatus of claim 25, wherein the server is for transmitting a form for inputting the data from the server to the terminal, and the terminal is for displaying the form at the display.

31. The apparatus of claim 30, wherein the server is for maintaining a web page comprising the form.

* * * * *